US007628996B2

(12) United States Patent
Haspel et al.

(10) Patent No.: US 7,628,996 B2
(45) Date of Patent: Dec. 8, 2009

(54) STERILE IMMUNOGENIC NON-TUMORIGENIC TUMOR CELL COMPOSITIONS AND METHODS

(75) Inventors: Martin V. Haspel, Seneca, MD (US); Nicholas Pomato, Frederick, MD (US); Michael G. Hanna, Jr., Frederick, MD (US)

(73) Assignee: Intracel Resources LLC, Frederick, MD (US)

( * ) Notice: Subject to any disclaimer, the term of this patent is extended or adjusted under 35 U.S.C. 154(b) by 445 days.

(21) Appl. No.: 10/370,081

(22) Filed: Feb. 21, 2003

(65) Prior Publication Data

US 2003/0228300 A1    Dec. 11, 2003

Related U.S. Application Data

(60) Provisional application No. 60/358,431, filed on Feb. 22, 2002.

(51) Int. Cl.
*A61K 35/12* (2006.01)
(52) U.S. Cl. .................................................. 424/277.1
(58) Field of Classification Search ........................ None
See application file for complete search history.

(56) References Cited

U.S. PATENT DOCUMENTS

| | | | |
|---|---|---|---|
| 4,878,891 A | 11/1989 | Judy et al. | |
| 5,300,433 A | 4/1994 | Hrinda et al. | |
| 5,484,596 A | 1/1996 | Hanna, Jr. et al. | |
| 5,532,141 A | 7/1996 | Holler | |
| 5,730,933 A | 3/1998 | Peterson | |
| 5,788,941 A | 8/1998 | Dalmasso et al. | |
| 5,837,233 A | 11/1998 | Granger | |
| 6,090,385 A | 7/2000 | Maes | |
| 6,136,306 A | 10/2000 | Granger | |
| 6,180,357 B1 | 1/2001 | Young et al. | |
| 6,218,166 B1 * | 4/2001 | Ravindranath et al. | 435/366 |
| 6,270,723 B1 | 8/2001 | Laugharn, Jr. et al. | |
| 6,299,873 B1 | 10/2001 | Smilowitz et al. | |
| 6,333,028 B1 | 12/2001 | Berd | |
| 6,406,699 B1 | 6/2002 | Wood | |
| 6,413,714 B1 | 7/2002 | Margolis-Nunno et al. | |
| 6,506,339 B1 | 1/2003 | Girardot et al. | |
| 6,699,483 B1 | 3/2004 | Dalgleish et al. | |

FOREIGN PATENT DOCUMENTS

EP        0151030 A2    8/1985
WO       WO 93/06867    4/1993

OTHER PUBLICATIONS

Definition of "excision" in Merriam-Webster Online Dictionary downloaded on Jan. 30, 2007 from the url, world wide web, m-w.com.*
Janicke et al (1994), Cancer Research, vol. 54, pp. 2527-2530.*
Hamer et al (1999), J Bone Joint Surg [Br], 81-B, pp. 342-344.*
Harris, J.E., "Adjuvant Active Specific Immunotherapy for Stage II and III Colon Cancer with an Autologous Tumor Cell Vaccine: Eastern Cooperative Oncology Group Study E5283", Journal of Clinical Oncology, vol. 18, No. 1, Jan. 2000, pp. 148-157.
Hanna, M.G. Jr., "Adjuvant Active Specific Immunotherapy of Stage II and III Colon Cancer with an Autologous Tumor Cell Vaccine: First Randomized Phase III Trials Show Promise", Vaccine, vol. 19, No. 17-19, Mar. 2001, pp. 2576-2582.
Hanna MG Jr, Zbar B, Rapp HJ., "Histopathology of tumor regression after intralesional injection of Mycobacterium bovis. I. Tumor growth and metastasis," J Natl Cancer Inst 48:1441-1455, May 1972.
Hanna MG Jr, Snodgrass MJ, Zbar B, Rapp HJ., "Histopathology of tumor regression after intralesional injection of Mycobacterium bovis. IV. Development of immunity to tumor cells and to BCG", J Natl Cancer Inst 51:1897-1908, Dec. 1973.
Hanna MG Jr, Peters LC., "Efficacy of intralesional BCG therapy in guinea pigs with disseminated tumor", Cancer 36:1298-1304, Oct. 1975.
Hanna MG Jr, Peters LC, Fidler IJ, "The efficacy of BCG-induced tumor immunity in guinea pigs with regional and systemic malignancy", Cancer Immunol Immunother 1:171-177, 1976.
Hanna MG Jr, Peters LC., "Immunotherapy of established micrometastases with bacillus calmette-guérin tumor cell vaccine", Cancer Res 38:204-209, Jan. 1978.
Hanna MG Jr, Peters LC., "Specific immunotherapy of established visceral micrometastases by BCG-tumor cell vaccine alone or as an adjunct to surgery", Cancer 42:2613-2625, Dec. 1978.
Hanna MG Jr, Brandhorst JS, Peters LC., "Active specific immunotherapy of residual micrometastasis: An evaluation of sources, doses and ratios of BCG with tumor cells", Cancer Immunol Immunother 7:165-173, 1979.
Peters LC, Hanna MG Jr., "Active specific immunotherapy of established micrometastasis: Effect of cryopreservation Procedures on Tumor Cell Immunogenicity in Guinea Pigs", J Natl Cancer Inst 64:1521-1525, Jun. 1980.
Peters LC, Brandhorst JS, Hanna MG Jr., "Preparation of immunotherapeutic autologous tumor cell vaccines from solid tumors", Cancer Res 39:1353-1360, Apr. 1979.
Hanna MG Jr, Peters LC., "Morphological and functional aspects of active specific immunotherapy of established pulmonary metastases in guinea pigs", Cancer Res 41:4001-4009, Oct. 1981.

(Continued)

*Primary Examiner*—Misook Yu
(74) *Attorney, Agent, or Firm*—Dickstein Shapiro LLP

(57) ABSTRACT

This invention relates to methods of removing bioburden from an aggregate of cells to obtain sterile cells that remain viable and immunogenic for the production of vaccines. This invention further relates to a method of eliciting an immune response to prevent a recurrence of metastases that involves preparing and administering a sterile vaccine derived from solid tumors. The vaccine is prepared by excising a solid tumor from a cancer patient, digesting the tumor cells with an enzyme to obtain dissociated cells, irradiating the dissociated cells to render the cells non-tumorigenic, and sterilizing the cells.

17 Claims, 4 Drawing Sheets

OTHER PUBLICATIONS

Hoover HC Jr, Surdyke M, Dangel RB, et al., "Delayed cutaneous hypersensitivity to autologous tumor cells in colorectal cancer patients immunized with an autologous tumor cell: Bacillus Calmette-Guérin vaccine", Cancer Res 44:1671-1676, Apr. 1984.

Hoover HC Jr, Surdyke MG, Dangel RB, et al., "Prospectively randomized trial of adjuvant active specific immunotherapy for human colorectal cancer", Cancer 55:1236-1243, Mar. 1985.

Hanna MG Jr, Peters LC, Hoover HC Jr., "Immunotherapy by active specific immunization: Basic Principles and Preclinical Studies", Biologic Therapy of Cancer Principles and Preclinical Studies, pp. 651-669, 1991.

Examination Report issued Jun. 26, 2007.

Peters, L.C. et al., "Preparation of Immunotherapeutic Autologous Tumor Cell Vaccines from Solid Tumors", Cancer Research, vol. 39, Apr. 1979, pp. 1353-1360.

* cited by examiner

STERILE IMMUNOGENIC NON-TUMORIGENIC TUMOR CELL COMPOSITIONS AND METHODS

This application claims the benefit of U.S. Provisional Application Ser. No. 60/358,431, filed Feb. 22, 2002, the entire disclosure of which is incorporated herein by reference.

FIELD OF THE INVENTION

The present invention relates generally to biological cell sterilization methods and resulting sterile cell products; and more particularly, but not by way of limitation, to cancer vaccines and methods for preparing sterile immunogenic and viable but non-tumorigenic tumor cell compositions.

BACKGROUND OF THE INVENTION

It is difficult to sterilize biological cell compositions for prophylactic and therapeutic purposes because the chemical, physical, or physiological properties of the cells can be significantly altered by variations in the cells' surrounding environment. For example, gas sterilization using, for example, ethylene oxide, is known to be toxic and also carcinogenic. Irradiation with about 1-3 mRads (megarads), while sufficient to kill microorganisms, can alter the structure of proteins, DNA, RNA, etc. and either biologically modify the cells or render the cells totally inactive for their intended immunogenic or other biological function. These difficulties are exasperated when it is important that any chemical or physical means employed achieve not only a high level of sterility but also substantially no reduction in the metabolic and immunogenic properties of the cells.

U.S. Pat. No. 5,484,596 ("the '596 patent") entitled "Active Specific Immunotherapy" relates to a method for treating human colon cancer patients with resectable solid tumors to inhibit recurrence and formation of metastases. The method comprises surgically removing colon tumor tissue from a human cancer patient, treating the tumor tissue to obtain tumor cells, irradiating the tumor cells (with 20,000 rads) to be viable but non-tumorigenic, preparing a vaccine comprising viable but non-tumorigenic tumor cells, and injecting the vaccine intradermally after the cancer patient's immune system has recovered from surgery.

By virtue of the origin of colon tumors within the large bowel, cancer vaccines produced by the process of the '596 patent are not sterile. Although the vaccine product (Onco-VAX®) prepared according to that patent has already been administered to several hundred human patients, regulatory authorities now require that such vaccine products must be sterile. To obtain an immunogenic cell preparation, the tumor cells must be viable and metabolically active. Thus any treatment to render the cells sterile must not unduly compromise the essential biological characteristics of the cells required for efficacy. What is needed is a process that renders cell preparations sterile, while maintaining viability and immunogenicity. Preferably, such a sterilization process can be easily integrated into existing product manufacturing processes.

The present invention is directed to achieving safe, sterile tumor cell compositions, without incurring substantial changes to the immunogenic properties of the tumor cells. These goals are not necessarily compatible. For example, sterilization can inactivate microbial infection but also can substantially inactivate mammalian cells; disinfectants kill microbes but can also kill mammalian cells; and radiation can render microbial infection inactive but can also substantially modify the immunogenic and other properties of mammalian cells. It is therefore desirable to provide a process for obtaining sterile non-tumorigenic tumor cell compositions which does not substantially interfere with essential metabolic and immunogenic properties of the cells.

SUMMARY OF THE INVENTION

The present invention provides a highly efficacious combination of chemical and physical means for removing and inactivating bioburden from tumor cells to obtain sterile cell compositions that remain viable and immunogenic for the production of therapeutic and prophylactic products. This sterilization treatment method is considered useful for a wide variety of cell types; however, it is considered to be particularly useful for sterilizing solid tumor tissue for the preparation of cancer vaccines, including, by way of example, the autologous colon cancer vaccine of the '596 patent.

This invention further relates to methods of treating cancer and preventing the recurrence of metastases by administering a sterile vaccine derived from solid tumors, including, but not limited to, colon carcinoma, renal carcinoma, breast carcinoma, lung carcinoma, and sarcomas, including osteosarcoma. In one embodiment, the present invention provides an integrated multiple step process beginning with an in situ tumor and resulting in a sterile tumor cell vaccine demonstrating no evidence of microbial growth.

According to a further embodiment, of the invention, an in situ colon tumor is forcefully washed with a wash solution containing saline and a detergent. Forceful washing may be achieved by aseptically fitting a sterile port onto a bag containing the wash solution and "squirting" such solution over the tumor and surrounding tissue. Suitable detergents include, e.g., Triton X-100, NP40 and Tween 80. The tumor may then be excised and transported, under controlled conditions, to a facility for vaccine preparation.

The excised tumor is then dissected, treated with a chemical disinfectant, and fragmented before digesting to release the individual tumor cells. The concentration of disinfectant and duration of treatment are chosen so as to enhance antimicrobial activity while minimizing cytotoxicity. Suitable disinfectants include, but are not limited to, Clorpactin® (sodium oxychlorosene) (United-Guardian, Inc.), sodium hypochlorite, and Oxygene® (stabilized chlorine dioxide) (Oxyfresh Worldwide, Inc.). After disinfection, the tumor is fragmented and digested by use of a dissociation enzyme, preferably in the presence of antibiotics and one or more anti-mycotics. Examples of suitable dissociation enzymes include collagenase and trypsin. Antibiotics and anti-mycotics for use during dissociation include aminoglycoside antibiotics (such as gentamicin), β-lactam thienamycin antibiotics (such as Primaxin® (imepenem) (Merck & Co., Inc.)), quinolone antibiotics (such as Levaquin® (levofloxacin) (Ortho-McNeil)), and anti-mycotics (such as amphotericin B).

After dissociation, the suspended tumor cells may be cryopreserved by controlled rate freezing at about −1° C./minute to a temperature of about −80° C. The tumor cells, preferably while still frozen, are then irradiated with a dose sufficient to inactivate microorganisms and tumorigenicity, while not adversely affecting the viability, metabolic activity, and immunogenicity of the cells. The irradiation dose is about 100,000-200,000 rads of gamma radiation; preferably a range of about 150,000-200,000 rads; and more preferably about 190,000-200,000 rads. The irradiated cells are maintained in a cryogenic state until thawed prior to administering to a patient.

Patients may be administered the thawed sterile cells in the form of a cancer vaccine by intradermal injection, preferably in an amount of about $10^7$ viable tumor cells per dose to elicit an immune response and prevent the recurrence of metastases. The dose typically contains tumor cells having at least 80% viability as measured by Trypan Blue exclusion. The vaccine may be administered to a patient in several doses, including one dose per week for a minimum of three weeks. Doses may be combined with an adjuvant or immunostimulator in physiological saline in order to further boost the immune response. Examples of suitable adjuvants and immunostimulators include BCG (Bacillus of Calmette and Guerin (Organon, Inc.)), *Corynebacterium parvum* (GlaxoSmithKline), "helper" antigens, such as KLH (keyhole limpet hemocyanin (Intracel Corp.)), and lymphokine-cytokines, such as GM-CSF (granulocyte-macrophage colony-stimulating factor (Leukine®) (Schering-Plough)) and interferon (Avonex® (Biogen, Inc.)).

According to a particularly preferred embodiment, the sterilization process of the invention includes: (1) forceful washing of an in situ colon tumor and surrounding tissue with four 500 mL quantities of sterile normal saline, at least one of the saline washes containing 1% Triton X-100; (2) transport of the tumor at a temperature of 0°-6° C., which permits at least a 48 hour interval between surgical excision and the initiation of the dissociation process; (3) treatment of the tumor pieces before fragmentation for two minutes with 0.4% Clorpactin®; (4) dissociation of the tumor in the presence of gentamicin, Primaxin®, Levaquin®, and amphotericin B; and (5) irradiation of the dissociated cells, while frozen, with 200,000 rads. A bioequivalency study was initiated using the resulting sterile tumor cells. The criterion for positive immunogenicity was a Delayed Cutaneous Hypersensitivity ("DCH") response of $\geq 5$ mm to the third injection. To date, twelve patients have been treated. All of the patients have had DCH responses (average 14.6×13.4 mm) that exceeded the criterion for a positive immunogenic response. Depending upon the diagnostic staging of the cancer, the patients received a fourth treatment 5-9 months after the first injection. Five of the six patients to receive a fourth treatment had an average DCH response of 15.1×15.1 mm. These responses are indicative of the development of long-term immunity to the sterilized tumor cells and thus immunity to recurrence of colorectal carcinoma.

These and other advantages and features of the invention will be more readily understood from the following detailed description which is provided in connection with the accompanying drawings. While the illustrative examples below discuss colon tumors and autologous colon cancer vaccine preparation, the teachings of the invention are applicable to any solid tumor cells that are intended to undergo sterilization and yet remain viable, metabolically active, non-tumorigenic, and immunogenic.

DETAILED DESCRIPTION OF THE INVENTION

Figure 1:
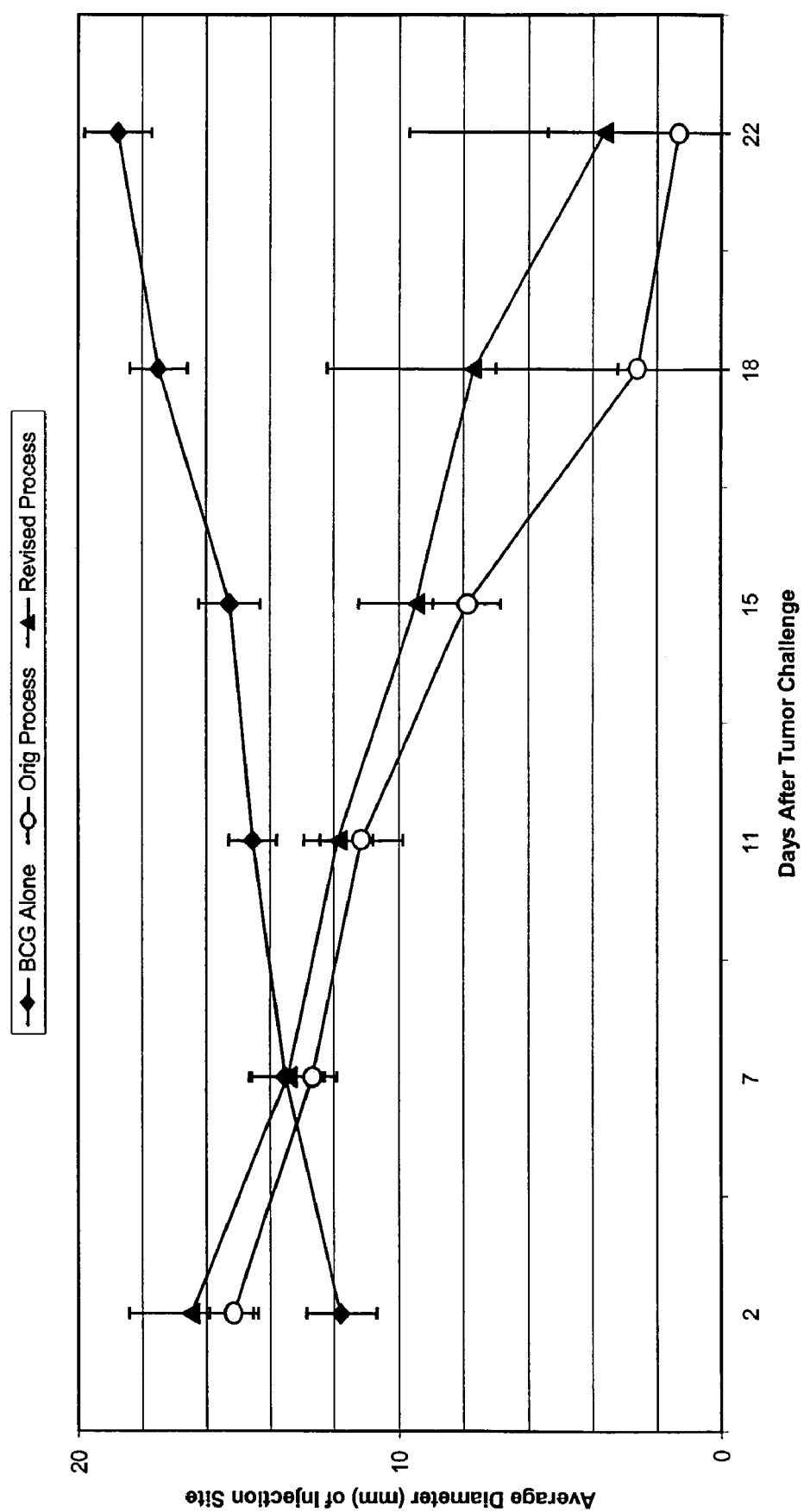
FIG. 1 demonstrates the immunogenic efficacy of vaccine cells, tested in the experimental model used to develop OncoVAX®, prepared according to the invention, in comparison to the efficacy of vaccine cells prepared by the original non-sterile OncoVAX® process. As can be seen, the improved sterilization process had no negative impact on efficacy. As demonstrated in Example 6, these data are confirmed and extended by a study of human patients treated with OncoVAX® prepared according to the invention.

The word "sterile" or "sterilization" for purposes of this invention, is used to indicate that the tissue or cells have been rendered free of all detectable bacteria, yeasts and fungi. This is in accordance with all applicable regulatory requirements.

Operating room aseptic procedures can reduce the possibility of extraneous contamination of excised tumor cells. With regard to colon tumors, patient antibiotic treatment and bowel preparation prior to surgery and colon resection can further reduce endogenous bioburden and fecal contamination. However, because of the anatomical location and the presence of enteric microorganisms, such measures, while useful, are only a first step toward rendering the tumor sterile as necessary for vaccine development.

The preferred place for performing the initial pathological processing of tumor cells is the aseptic operating room or another controlled environment. Here, washing the colon or other organ containing the tumor and the in situ tumor can reduce bioburden prior to excision of the tumor from the colon by removing residual fecal, mucinous, or other extraneous material. Forceful washing is preferred, and can be achieved by washing the colon, for example, by using a squirt bottle to project a sterile wash solution against the surface of the tumor and surrounding tissue. The wash solution may be, for example, sterile normal saline and a detergent. The detergent must not unduly interfere with subsequent histological techniques including immunohistochemistry. Suitable detergents include Triton X-100, NP40, and Tween 80, although various others may be used.

For forceful washing of the in situ tumor, intravenous saline available in 500 mL flexible bags can be aseptically fitted with a sterile port to transform the bag into a squirt bottle. The colon, for example, can be held vertically or horizontally (with the area of the colon containing the tumor slightly elevated) and several 500 mL washes can be forcefully projected onto the tumor to remove fecal material that could further contaminate the tumor during subsequent dissection. Various amounts of wash solution and detergent and/or antibiotic may be employed using the teachings herein, including different wash conditions (pouring wash solution versus forceful washing), different numbers of wash cycles, and different wash solutions and amounts. We have found that four 500 mL washes of the in situ tumor by forcefully squirting saline and one 500 mL wash by forcefully squirting 1% Triton X-100 in saline provide sufficient removal of bioburden for subsequent tumor processing.

After washing the tumor in situ the pathologist may remove and dissect the tumor in the operating room (or other controlled environment) for subsequent transport to a vaccine manufacturer or other facility for further processing. The dissected tumor may be transported by any suitable method that maintains the proper temperature conditions throughout the transport. Preferably, an antibiotic such as gentamicin is added to the transport medium (e.g., Hank's Balanced Saline Solution (HBSS) containing 50 µg gentamicin per ml (HBSS/G)) prior to tumor transport or storage. We have found that dissected tumor can be transported from the surgical hospital to a distant facility over a period of about 48 hours or more, if an appropriate antibiotic is added to the medium and the dissected tumor is maintained at a temperature in the range of about 0° to 6° C.

A further reduction of surface contamination of the dissected tumor is achieved by disinfecting the tumor pieces prior to further fragmentation and dissociation. Chemical disinfectants, however, are general acting and therefore do not discriminate between mammalian and bacterial (or fungal) cells. Consequently, unlike treatment with antibiotics, the use of chemical disinfectants at microbicidal concentrations on dissociated tumor cells can result in unacceptable levels of toxicity for the tumor cells.

Excised tumors typically encompass several pieces as pathologists frequently cut the tumor to determine the deepest margin of penetration. These pieces may be further dissected, preferably in the presence of HBSS/G, to remove any extraneous non-tumor and necrotic tissue before conducting the disinfection step. The luminal surface of colon tumors typically contains the greatest amount of bioburden. Chemical disinfectants kill any exposed microorganisms together with the exposed tumor cells. In this manner, use of a disinfectant can chemically "cauterize" the outer portion of the dissected tumor pieces where the superficial bioburden is located. Such treatment of the dissected tumor prior to fragmentation disinfects the surface of the tumor pieces, while exposing a minimum surface area to the disinfectant. The deeper aspects of the tumor are thus unaffected, and thereby remain a source of viable tumor cells. Because of the polypoid nature of colon tumors with its multiple invaginations, there are areas where bacteria are trapped and protected from the disinfectant. Thus, the inherent bioburden may be reduced significantly, but not totally eliminated, by treatment with an appropriate disinfectant.

Various disinfectants and amounts may be used, including Carrel-Dakin solution (buffered 0.5% sodium hypochlorite) and Clorpactin® at various concentrations and exposure times. In one embodiment, dissected tumor pieces are exposed to 0.4% Clorpactin®, for 2 minutes. Disinfection can be conveniently carried out by any suitable method, including placing the dissected tumor pieces into a flask containing a disinfectant solution (e.g., about 125 mL of 0.4% Clorpactin®) and then by shaking for about two minutes at about 200 rpm on a rotating platform shaker. For colon tumor pieces, we have found that a single two minute treatment with about 0.4% Clorpactin® provides beneficial results prior to tumor fragmentation and dissociation. Normally, after the chemical treatment, the chemical disinfectant is removed by washing with saline.

The possibility of re-contamination is reduced by appropriate aseptic techniques, such as line clearance and sanitization of biological safety cabinets (BSC) after tumor disinfection procedures. All steps that may result in exposure of the product to the environment should be conducted in a BSC and all materials sprayed or wiped with 70% iso-propyl alcohol, or other appropriate disinfectant, prior to placing the materials in the BSC.

The disinfected tumor pieces may then be fragmented by any suitable method to obtain smaller pieces (such as about 2-4 mm$^2$) for the dissociation process. Fragmentation facilitates the dissociation process by exposing more tumor surface area to the dissociation enzyme. The fragments may be rinsed with, e.g., HBSS/G and maintained at about 0° to +6° C. in a Kryorack until the tumor has been completely fragmented and an appropriate amount, e.g., about 3.0 grams, of tumor fragments are obtained for subsequent digestion by a dissociation enzyme to free individual tumor cells.

Prior to dissociation, the tumor pieces may be washed with physiological solution (e.g., HBSS) containing an antibiotic (e.g., gentamicin) (HBSS/G). To carry out the dissociation process, tumor pieces that have been trimmed and minced into fragments are transferred to a flask or other suitable container and incubated with an enzyme dissociation medium for a time sufficient to form a suspension of tumor cells. The duration depends on the concentration and selection of enzyme, and the number of dissociation cycles. The enzyme is typically a collagenase-DNase solution (e.g., 30-40 ml of 0.14% (200 units/mL) Collagenase Type 1 (Advance Biofacture) and 0.1% (500 Kunitz units/ml) deoxyribonuclease type 1 (Sigma D-0876)) in HBSS, but any suitable dissociation enzyme solution may be used. Sterile HBSS together with gentamicin or another antibiotics may be used to wash the cell suspension obtained by enzymatic dissociation. In one embodiment, the enzyme dissociation medium (30 mL) is 0.14% collagenase, 0.1% DNase in HBSS with gentamicin (HBSS/G). For tumor fragments of about 2-4 mm$^2$, we have found that three dissociation cycles of 35 to 45 minutes at 36-38° C. can produce about $7.2 \times 10^7$ tumor cells or more. Following each dissociation cycle, the cells may be centrifuged, rinsed, and resuspended in sterile HBSS/G.

The resulting cell suspension also may be sieved if desired using a nylon mesh to remove any cell clumps. A closed system, such as pediatric transfusion kit, may be employed to further reduce any possibility for contamination. The resulting dissociated cells are then vialed and a random quality control sample is retained for testing and release of tested product for quality control purposes.

Microorganisms trapped within tumor invaginations are typically released during fragmentation and enzymatic dissociation. Enzymatic dissociation also occurs under conditions favorable for the growth of enteric microorganisms. We have found that the presence of antibiotics during dissociation can reduce bioburden released during dissociation and inhibit the further growth of microorganisms during dissociation. Antibiotics typically act over an extended period of time. Because the dissociation process is of relatively short duration, however, certain antibiotic/anti-mycotic cocktails are preferred for use during incubation with the dissociation enzyme. Preferred antibiotics and anti-mycotics for incubation with the enzyme during dissociation include an antibiotic effective against anaerobes (such as Primaxin®), an antibiotic effective against gram positive aerobes (such as an antibiotic of the quinolone class, e.g., levofloxacin), and an anti-mycotic for its action on yeasts, which are unaffected by antibiotics. A preferred anti-mycotic is amphotericin B. In one embodiment, the enzyme dissociation medium contains 25 μg of Levaquin®, 100 μg of Primaxin®, and 1 μg of amphotericin B, per mL of enzyme dissociation medium.

The dissociated cell suspensions are then centrifuged for a further wash prior to cryopreservation. After centrifugation, the pellet may be resuspended in biological substance vials in an appropriate volume of HBSS/G together with freezing medium (2× freezing medium containing 15% dimethylsulfoxide (DMSO) and 1% human serum albumin (HSA)). The cells are placed into cryovials and cryopreserved by controlled rate freezing at about −1° C./minute to a temperature of about −80° C. The cryopreservation cycle is not initiated until the vials and the freezer chamber have been equilibrated to a temperature of +4° C. The resulting frozen suspensions may be stored in, e.g., liquid nitrogen. The cells are typically maintained in a cryopreserved state until being thawed for administering to a patient. They should be transferred on dry ice as soon as possible from the controlled rate freezer to a liquid nitrogen storage system. The frozen biological substance is then released for irradiation of the frozen vials.

The irradiation dose is selected to not only render the tumor cells non-tumorigenic (typically about 20,000 rads), but also to inactivate any residual bioburden in the dissociated cell suspensions. Megarad doses of radiation, however, are incompatible with live, metabolically active mammalian cells. A preferred dose according to the present invention is about 100,000 to 200,000, more preferably about 150,000-200,000, and most preferably 190,000-200,000, rads of gamma radiation. This provides an adequate microbicidal dose of radiation of the vials of frozen tumor cells, that, together with the other bioburden reducing steps of the process, renders the cells sterile. Irradiating tumor cells while frozen also has the advantage of permitting the irradiation prior to testing and release of the cells for patient treatment. This is in contrast to methods of the '596 patent, which applied 20,000 rads to liquid cell suspensions just prior to patient dose formulation.

In one embodiment of the present invention, the frozen vials of dissociated tumor cells are removed from the liquid nitrogen storage system and placed on a 2-5 cm bed of dry ice within the irradiation container of the irradiator. The vials are then completely covered with dry ice to fill the irradiation container. The irradiation cycle begins and is paused every two hours, if necessary, to refill the container with dry ice. After 200,000 rads are applied, the vials are returned to liquid nitrogen.

Irradiation preferably takes place at one or more centralized manufacturing centers. This eliminates the requirement for an irradiator at each outpatient site and allows for process control by the vaccine or other sterile cell product manufacturer. Various quality control tests may be performed to ensure sterile, safe and efficacious vaccine products. Such tests on randomly selected quality control samples prior to product release will typically include sterility, cell enumeration, endotoxin, identity, and potency tests.

Final vaccine formulation can be performed by a pharmacist with limited facility requirements because frozen irradiated cells can be transported, after complete quality control procedures have been performed, to the pharmacist, patient care provider, or other final user of the vaccine to administer the product to a patient in need of treatment.

The first step in vaccine formulation will typically be thawing the sterile immunogenic non-tumorigenic tumor cells. Frozen tumor cells may be thawed after radiation by any suitable method including a water bath. A heat block is preferred to minimize the possibility of contaminating the tumor cell vials with water-borne contaminants. At this point, the thawed cells may be further washed with HBSS by successive cycles centrifugation and resuspension in fresh HBSS. Various techniques may be selected given the teachings herein to prepare formulations for administering to patients pursuant to various dosing regimes, for example, those disclosed in the '596 patent. In a particularly preferred embodiment, $10^7$ viable sterile colon tumor cells as prepared by the above methods are injected intradermally into the cancer patient from whom the tumor had been obtained. Three doses of this autologous vaccine are injected at weekly intervals. The first two injections also contain about $10^7$ BCG organisms; the third injection does not contain any BCG. Not taught in the '596 patent is the addition of a fourth booster injection, comprised of the autologous tumor cells without any BCG, that is administered five or more months after the first treatment.

The sterile cell suspensions may be readily transported on cold packs to an outpatient clinic and administered according to specific dosing and treatment regimes indicated by the manufacturer and patient care provider.

Example 1

Washing of the Colon and Tumor In Situ Prior to Dissection

Intravenous normal saline (unlike HBSS) is available in 500 mL flexible bags. By aseptically fitting a sterile port (for example a Combi-port) into the bag, the bag is essentially transformed into a squirt bottle. By squeezing the bag, a stream of saline may be squirted with force and directed on the tumor and surrounding colonic mucosa.

For the first wash, the colon was held vertically and washed with 500 mL of saline beginning with the top and working downwards. In preliminary experiments, the second 500 mL wash consisted either of normal saline or 1% Triton X-100 (in normal saline) and was directed to the tumor and its immediate adjacent area. This wash was also performed while the colon was held vertically. The colon was then held horizontally with the area of the colon containing the tumor being slightly elevated. Additional washes (2-3), each consisting of 500 mL of saline, were then directed to the tumor. The run-off from each wash was collected in a separate sterile basin and assayed, providing an indirect measurement of the removal of bioburden. When available, the tumors were dissociated and the cell suspension (prior to cryopreservation) was assayed for bioburden providing direct evidence of the efficacy of the procedure.

Figure 2:
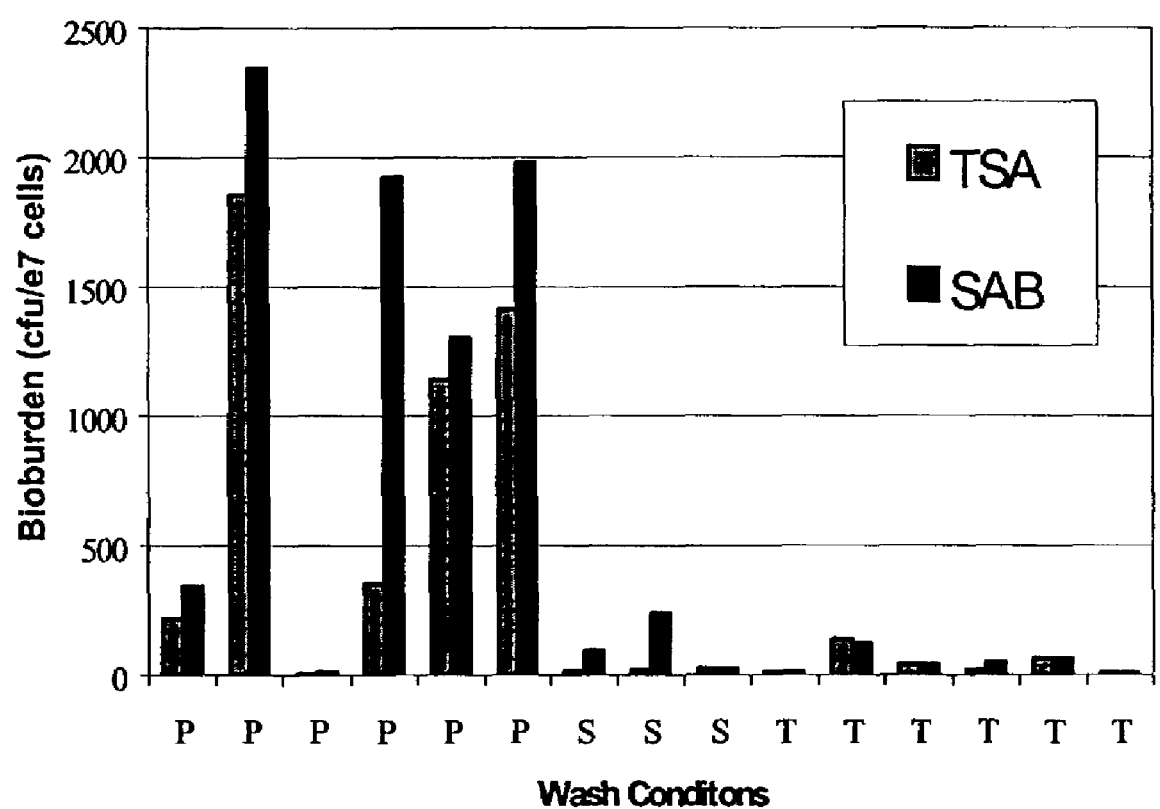
FIG. 2 demonstrates the effect of wash conditions on the bioburden of biological substances. Fifteen tumors were washed, in situ either by pouring HBSS/G on the tumor (P), by squirting the tumor with saline alone (S) or with saline in combination with Triton X-100 (T). The tumor tissue was then dissociated. The bioburden in the cell suspension was assayed using the membrane filtration method and plated on TSA-SB and SAB plates. The bioburden is expressed as colony forming units (CFU) per $10^7$ tumor cells, approximately one dose of OncoVAX®.

For the evaluation of the wash method, a direct determination of the bioburden was made, that is, the number of microorganisms in the cell suspension after dissociation was quantified. As seen in FIG. 2, higher bioburden (expressed as colony forming units CFU per $10^7$ tumor cells) was observed in the cell suspensions dissociated from tumors that were washed by pouring HBSS/G over the colon and colon tumor than from tumors squirted with saline alone or with saline in combination with Triton X-100. Clearly since the volumes used for the forceful washing procedure were greater (2000 or 2500 mL) than the poured saline method (1000 mL) it is not possible to attribute how much of the decrease is due to volume or method of application. It is, however, clear that taken in toto, the newer forceful washing method proved to be superior.

Figure 3:
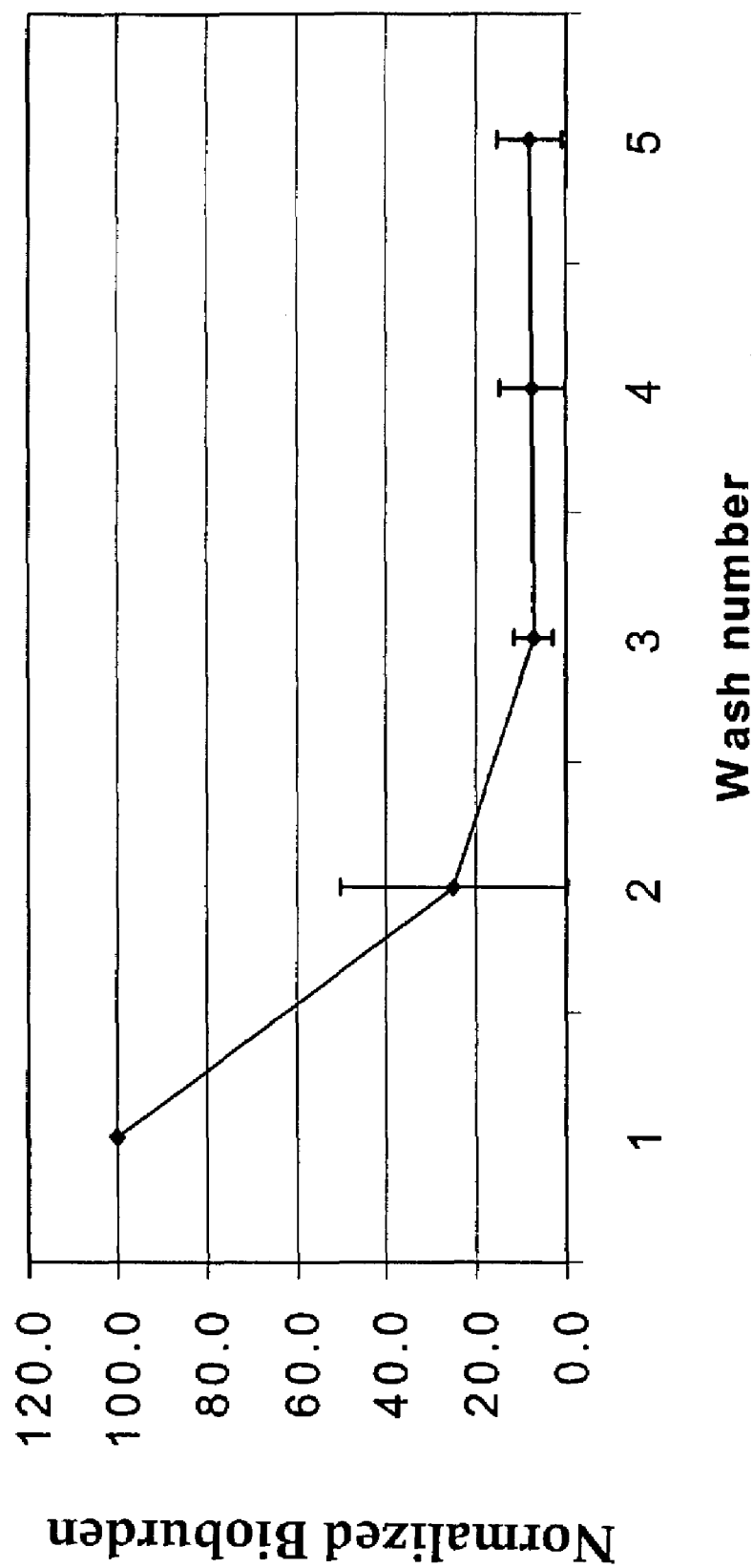
FIG. 3 demonstrates the effect of the number of tumor wash cycles, using only saline, on bioburden. Five tumors were washed five times prior to dissection using saline. The run-off from each wash was collected separately and assayed for bioburden by plating directly on TSA-SB plates. For each tumor, the raw colony counts obtained for each wash were divided by the CFU in the first wash, to normalize the data. The mean and the standard deviations of the normalized data are plotted.
Figure 4:
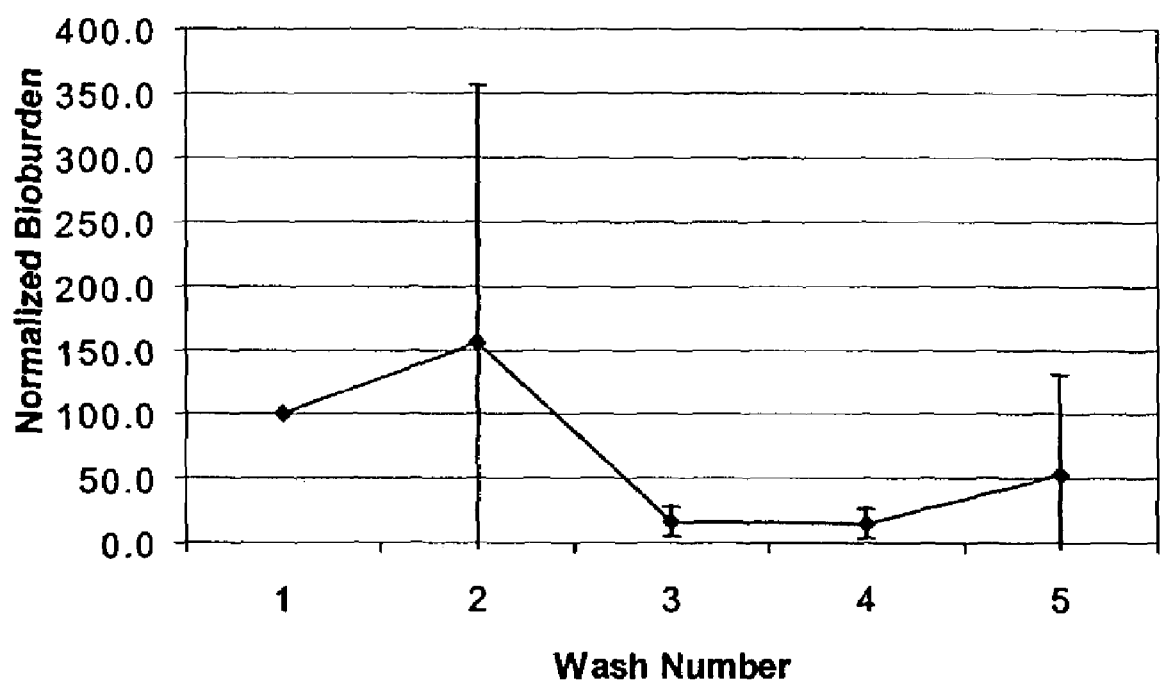
FIG. 4 demonstrates the effect of the number of tumor wash cycles, using saline and Triton X-100, on bioburden. Five tumors were washed five times prior to dissection. Washes one, two, three, four, and five contained saline. Wash number two was 1% Triton X-100 in saline. The run-off from each wash was collected separately and assayed for bioburden by plating directly on TSA-SB plates. For each tumor, the raw colony counts obtained for each wash were divided by the colony counts in the first wash, to normalize the data. The mean and the standard deviations of the normalized data are plotted.

The wash procedure occurs prior to dissection. Since the wash step is included in the process to remove fecal material that could further contaminate the tumor during the dissection procedure, it would be inappropriate to subdivide the tumor by dissection prior to washing to achieve a comparative study of bioburden in the dissociated cells. Furthermore, it is not possible to wash half of the tumor with saline alone and half with Triton X-100 in combination with saline or with fewer or more washes in situ. Consequently, it was not possible to perform a comparative study on the same patient material. The determination of bioburden in the run-off from each wash provides evidence of the efficacy of the different wash solutions. The absolute bioburden levels in each experiment varied widely because the amount of fecal flora varies from patient to patient. To assess the relative effectiveness of each wash, the bioburden values of each wash was divided by the bioburden in wash # 1 to normalize the data. When saline alone was used (5 tumors), there was a consistent decrease in the quantity of bioburden in the run-off (FIG. 3). The average for wash #2, was 25% of the bioburden present in wash #1 (range of 3.6% to 74%). The average bioburden in wash #3 was 7% of wash #1 (range 0.6 to 13%). By contrast, in the case of two of the five tumors treated with Triton X-100, there was more bioburden present in the second wash containing Triton X-100 (241% and 513%) than in the first wash (FIG. 4). The bioburden in the third wash was again lower. These data are suggestive of enhanced removal of bioburden by the Triton X-100. We propose to use Triton X-100 at the second wash step. The majority of the bioburden that could be removed by washing, was removed by the first three washes; there was little contribution by the fourth or fifth washes.

Based upon the studies described above, we adopted a washing procedure of forcefully squirting, rather than pouring, the wash solutions on the colon and tumor. There is sufficient support for the addition of the surfactant Triton X-100 to one of the wash solutions. Thus, the preferred pre-dissection processing includes an initial wash with 500 mL of saline, followed by 500 mL of 1% Triton X-100 and concluded with two addition (500 mL) washes with saline alone.

Example 2

Chemical Disinfection of Colon Tumors Prior to Enzymatic Dissociation

For pathological staging purposes, the pathologist cuts the tumor to determine the deepest margin of penetration. Consequently, the excised tumors are comprised of several pieces of tumor tissue. The tissue was dissected to remove extraneous non-tumor and necrotic tissue. The trimmed tumor pieces were further subdivided to achieve homogeneity and divided into two to four groups for processing according to the experimental design. The tissue was divided as evenly as possible among the samples, taking care to make the tumor pieces in the experimental groups appear as identical as possible. The trimmed pieces were added to a tube containing 40 mL of disinfectant and then treated by shaking for 2 minutes at 200 rpm on a rotating platform shaker. The trimmed tumor pieces were then washed three times with HBSS and then dissociated. The amount of tumor dissociated was determined by weighing the tumor fragments prior to dissociation and after completion of the dissociation cycles. After dissociation, the tumor cell suspension was sampled for percent tumor cell viability, number of viable tumor cells, tumor cell potency and bioburden. The yield was defined as the number of viable tumor cells obtained per gram of tumor that was actually dissociated. The bioburden was normalized to $CFU/10^7$ viable tumor cells, approximately one dose of product.

In initial experiments, concentrations of sodium hypochlorite that were effective in reducing the bioburden, also significantly reduced the tumor cell yield relative to the control. At the concentrations tested, Clorpactin® reduced the bioburden in the sample, with a more moderate reduction in tumor cell yield relative to the control. The treatment of the trimmed tumor pieces with disinfectants reduced the bioburden but did not render the tumor cell suspension sterile.

The original intent of the disinfectant experiments was, as a single step, to render the dissociated tumor cells sterile. The approach was changed to consider disinfection as part of an integrated, multi-step process to render the product sterile. The disinfection of the tumors prior to dissociation was therefore revisited and the initial results obtained with Clorpactin® were confirmed and extended by additional experimental study. In addition, another antiseptic (chloroxylenol) that operates by a different biological mechanism, was also evaluated. Chloroxylenol, or PCMX, is the active ingredient of the surgical scrub, Techni-Care® (Care-Tech Labs., Inc.).

The results of this study are presented in Table 1. Tumor sample 500-0051-KNO was washed with saline, a second wash with 1% Triton X-100 and followed by three additional saline washes (see Example 1). The resultant bioburden was below the limit of detection of the assay. In order to evaluate the ability of a disinfectant to remove bioburden, one to two logs of bioburden must be detectable in the control sample. In order to maximize the possible bioburden in the tumors and present a greater challenge to the disinfectant, the following modifications to the procedure were made: the tumors were minimally washed (one 500 mL quantity) prior to pathological dissection; the dissociations were performed in the absence of gentamicin.

Treatment of the trimmed tumor pieces with Clorpactin® resulted in bioburden reductions to almost three orders of magnitude with only moderate losses in cell yield relative to the control. The control sample for tumor 500-052-EVA had an unusually low cell yield for the control, and thus aberrantly high percent yields (relative to this control) for the experimental samples. The manufacturer's recommended dosage of Clorpactin® is 0.2%-0.4%. When used at 0.8% in these studies, no further reduction in bioburden was observed; however there was a further reduction in the yield of viable tumor cells. For this reason, 0.4% Clorpactin® was selected as the working concentration for further study. The occasional higher levels of bioburden in the 0.8% Clorpactin® treated samples was probably due to the inherent difficulty in dividing the tumor pieces into equal portions that had identical levels of bioburden. Despite little or no microbiocidal effect, PCMX was more cytotoxic than Clorpactin® resulting in a significantly reduced yield.

The clinical use of Clorpactin® involves flushing the affected area with fresh disinfectant. Thus, as the active ingredient, chlorine, is dissipated, fresh disinfectant is applied to the area. The final studies compared two successive two minute treatments, each with fresh 0.4% Clorpactin®, with the normally performed single two minute treatment. No advantage for two treatments was observed.

Based on these studies, a single, two minute treatment of the tumor pieces with 0.4% Clorpactin® prior to fragmentation and dissociation was implemented as part of the preferred integrated, multistep process to render the tumor cells sterile.

TABLE 1

Disinfection of Tumors Prior to Dissociation

| Patient Sample | Treatment | VIABILITY (%) | Yield (%) | Potency (%) | Bioburden (CFU/107 Cells) & (% Reduction) |  |  |  |  |  | Sterility1 |  |
|---|---|---|---|---|---|---|---|---|---|---|---|---|
| | | | | | TSA-SB4 Aerobic | | TSA-SB Anaerobic | | SAB-CM5 Aerobic | | TSB2 | FTG 3 |
| 500-0051-KNO | Control (HBSS) | 94 | 100 | 97 | <44 | — | <44 | — | <44 | — | F | P |
| | 0.4% Clorpactin ® | 91 | 132 | 94 | <49 | (*) | <49 | (*) | <49 | (*) | P | P |
| | 0.33% PCMX | 94 | 201 | 97 | <34 | (*) | 136 | (*) | <34 | (*) | F | F |
| 500-0052-EVA6 | Control (PBS) | 90 | 100 | 98 | 105,000 | — | 117,000 | — | 89,000 | — | F | F |
| | 0.4% Clorpactin ® | 90 | 346 | 99 | 3910 | (96%) | 3890 | (97%) | 207 | (>99%) | F | F |
| | 0.8% Clorpactin ® | 93 | 272 | 96 | 7100 | (93%) | 8870 | (92%) | 4452 | (95%) | F | F |
| 500-0053-VBO6 | Control (HBSS) | 91 | 100 | N/D | 10 | — | 1100 | — | 10 | — | F | P |
| | 0.4% Clorpactin ® | 94 | 90 | N/D | <11 | (0%) | 343 | (69%) | ≦11 | (0%) | F | F |
| | 0.8% Clorpactin ® | 96 | 67 | N/D | <13 | (0%) | 1364 | (*) | ≦13 | (0%) | F | F |
| | 1.5% PCMX | 89 | 35 | N/D | <27 | (0%) | 1490 | (*) | ≦27 | (*) | F | P |
| 500-0054-ETA6 | Control (HBSS) | 93 | 100 | 99 | 33 | — | 68 | — | ≦17 | — | F | F |
| | 0.4% Clorpactin ® | 95 | 100 | 98 | <23 | (30%) | <23 | (66%) | ≦23 | (*) | F | F |
| Roc-00-00016 | Control (HBSS) | 95 | 100 | 97 | 160 | — | >300 | | ≦2 | — | F | P |
| | 0.4% Clorpactin ® One treatment | 96 | 158 | 97 | 2 | (99%) | 294 | (*) | ≦2 | (*) | F | P |
| | 0.4% Clorpactin ® 2 treatments | 90 | 67 | 98 | ≦2 | (99%) | 3800 | (*) | ≦2 | (*) | F | F |
| Roc-00-0002 | Control (HBSS) | 91 | 100 | 99 | ≦2 | — | ≦2 | — | ≦2 | — | P | F |
| | 0.4% Clorpactin ® One treatment | 92 | 164 | 100 | ≦2 | (*) | ≦2 | (*) | ≦2 | (*) | P | P |
| | 0.4% Clorpactin ® 2 treatments | 90 | 99 | 97 | ≦2 | (*) | ≦2 | (*) | ≦2 | (*) | F | P |

1. Sterility was scored as Pass (P) (no evidence of microbial growth) and Fail (F) (Microbial growth)
2. TSB, Tryptic Soy Broth
3. FTG, Fluid Thioglycollate Broth
4. TSB-SB, Tryptic Soy Agar containing sheep blood
5. SAB-CM, Sabouraud's Dextrose Agar containing chloramphenicol
6. These tumors were minimally washed in situ and did not contain gentamicin during dissociation to maximize possible bioburden.
*The percent reduction could not be calculated because either there was no bioburden detected in the untreated control or because the level of bioburden in the treated sample was higher than that in the control Example 3

Effect of the Presence of Antibiotics During Dissociation of Colon Tumors

Enteric microorganisms trapped within invaginations in the colon tumor are released during the process of enzymatic dissociation. Furthermore, the enzymatic dissociation process occurs under conditions (37° C.) that are favorable for the growth of enteric microorganisms. For these reasons, the effect of the addition of antibiotics to the dissociation enzyme solution and the addition of to other process solutions was investigated.

Antibiotics are normally used over an extended period of time. The first series of experiments was designed to evaluate the efficacy of various antibiotics over a short exposure period. The next series of experiments examined the effectiveness of the antibiotics when included in the dissociation enzyme solution.

Appropriate test microorganisms were incubated with the antibiotic for varying periods of time and at 4° C. or 37° C. "Untreated" controls were incubated with HBSS. After completion of the treatment, the samples were assayed for bioburden by the membrane filtration method on Tryptic Soy agar containing 5% sheep blood (TSA-SB) and Sabouraud's dextrose medium (SAB). The SAB medium used in these experiments for the detection of fungi did not contain chloramphenicol and therefore could also support the growth of bacteria.

Gentamicin (50 µg/mL) was present in all solutions including the HBSS used to suspend the cells prior to mixing (with an equal volume) of gentamicin-free cryoprotective medium. Three other antibiotic-antimycotic solutions were added only to the collagenase-DNase solution used to dissociate the tumor. The HBSS used to wash the cell suspension obtained by the enzymatic dissociation contained only gentamicin. The additional antibiotics used in these experiments were imipenem (Primaxin®) (100 µg/mL), levofloxacin (Levaquin®) (25 µg/mL) and amphotericin B (1 µg/mL). These concentrations were determined on cultured cells, spiked with test microorganisms, looking for cytotoxicity and antimicrobial activity.

Colon tumor pieces were washed in HBSS containing gentamicin, trimmed free of non-tumor or necrotic material and minced into fragments. The fragments were equally distributed into three flasks. One replicate of fragments was dissociated in the absence of all antibiotics to reproduce the conditions used to produce the vaccines used in earlier studies. The cells were subsequently washed with HBSS that was free of any gentamicin. The second set of fragments was dissociated in the presence of gentamicin. The HBSS used to wash the dissociated cells contained gentamicin. The third replicate was dissociated in the presence of gentamicin and the other test antibiotics. After completion of each dissociation cycle, the cells were resuspended and washed with HBSS that contained only gentamicin.

For the first four tumors processed, a portion of the cell suspension dissociated in the presence of gentamicin or gentamicin with other antibiotics was also incubated for an additional hour (after completion of the dissociation) with the same antibiotic(s). This additional incubation was evaluated for increased reduction of bioburden.

Gentamicin, because of its heat stability and broad antibacterial spectrum, is preferred for use during tumor transport and in wash solutions. Gentamicin is also included in the enzyme dissociation solution. Additional antibiotics were therefore selected on the basis of being complementary to gentamicin.

Anaerobes are the predominant microorganisms in the colon. Flagyl (2.5 and 5 µg/mL) was tested against *Bacteriodes vulgatus* and was found to be ineffectual under the aerobic incubation conditions used in these experiments. Lincomycin (Lincocin hydrochloride) (Sigma-Aldrich Co.) and Primaxin® were then tested against this anaerobe. When incubated either overnight (4° C.) or with an added incubation (i.e., 40 minutes at 37° C., 4° C. for 60 minutes followed by an additional 60 minutes at 37° C.), Primaxin® exhibited greater effectiveness than lincomycin. At 4° C., Primaxin® (100 µg/mL) induced a one log reduction, while lincomycin (up to 150 µg/mL) had no effect. When incubated under the extended conditions, Primaxin® induced a two log reduction while lincomycin induced a one log reduction.

Two members of the quinolone class of antibiotics norfloxacin (Noroxin® (Merck & Co., Inc.)) and levofloxacin (Levaquin® (Ortho-McNeil)) also were evaluated. In preliminary experiments, norfloxacin was tested against *Enterococcus faecalis* and *Pseudomonas aeruginosa*. Norfloxacin (12.5 to 50 µg/mL) incubated for one hour at 37° C. was highly effective against *P. aeruginosa* but was ineffectual against *E. faecalis*. When tested against *E. faecalis*, levofloxacin exhibited a minor but reproducible inhibition.

Amphotericin B was selected for action on yeasts and mold. Marked reduction in colonies of *Candida albicans* were observed one day after treatment with amphotericin B (0.5 to 1.0 µg/mL). This effect was, however, mycostatic rather than mycocidal; when observed after 8 days in culture, there was only slight inhibition at the higher concentration.

Thus, three antibiotics/anti-mycotics, in addition to gentamicin, were selected based upon their different spectra of sensitive microorganisms and were initially tested on laboratory strains. Imipenem (Primaxin® (Merck)) is a thienamycin antibiotic of the beta lactam class. It complements gentamicin particularly for anaerobes. Levofloxacin (Levaquin® (Ortho-McNeil)) is a member of the quinolone class of antibiotics. It complements both gentamicin and imipenem for gram positive aerobes. Finally, the anti-mycotic amphotericin B was included for its action on yeast, which are unaffected by antibiotics.

Seven tumors were dissociated by the regimen described above. As seen in Table 2, in all instances, the microbial bioburden was reduced, as detected by at least one of the test media, when the tumors were dissociated in the presence of gentamicin.

Four of the tumors dissociated in the presence of gentamicin had residual bioburden. Three of the cell suspensions (ROC-99-0035, ROC-99-0038, ROC-99-0039) produced from these four tumors in the presence of the complete panel of antibiotics had further, albeit small, reductions in bioburden. The bioburden in the fourth tumor cell suspension (ROC-99-0036 [SAB]) was unchanged. Inexplicably, in the case of a fifth tumor (ROC-99-0041 [TSA]), the bioburden was higher in the cell suspension produced in the presence of all of the antibiotics than in the presence of gentamicin alone.

As seen in Table 3, an additional incubation with gentamicin resulted in a minor further reduction in bioburden in two tumor preparations. Although an 80% reduction in CFU was detected on SAB (ROC-99-0035), this tumor cell suspension had greater than a three-fold increase in CFU when plated on TSA plates. A substantial increase in CFU on TSA plates was also observed with tumor cell suspension ROC-99-0036. Thus, a further incubation with gentamicin alone appears to be more detrimental than helpful. Further incubation with all of the antibiotics had, with the exception of ROC-99-0036 tested on SAB, no effect upon the bioburden. A significant reduction in bioburden was observed with this single sample.

The addition of gentamicin to the dissociation enzyme and post-dissociation process solutions results in a consistent reduction in endogenous bioburden present in colon tumors. There were further reductions in bioburden in some, but not all, of the tumors dissociated in the presence of the additional antibiotics.

TABLE 2

Effect of Antibiotics During Enzymatic Dissociation

Bioburden (CFU/107 Cells) and Percent Reduction of Bioburden

| Tumor ID | Medium | No Antibiotics | Gentamicin Only | All Antibiotics |
|---|---|---|---|---|
| ROC-99-0035 | TSA | $1.0 \times 10^3$ | $\leq 9$ ($\geq 99\%$) | $\leq 9$ ($\geq 99\%$) |
|  | SAB | $6.0 \times 10^2$ | 90 (85%) | 36 (94%) |
| ROC-99-0036 | TSA | $5.0 \times 10^3$ | $\leq 10$ ($\geq 99$) | $\leq 10$ ($\geq 99$) |
|  | SAB | $1.7 \times 10^3$ | $2.4 \times 10^2$ (86%) | $2.0 \times 10^2$ (88%) |
| ROC-99-0037 | TSA | 30 | $\leq 6$ ($\geq 80\%$) | $\leq 6$ ($\geq 80\%$) |
|  | SAB | 45 | $\leq 6$ ($\geq 87\%$) | $\leq 6$ ($\geq 87\%$) |
| ROC-99-0038 | TSA | $5.4 \times 10^2$ | $1.4 \times 10^2$ (74%) | 23 (8%) |
|  | SAB | 61 | $1.1 \times 10^2$ (0%) | 56 (92%) |
| ROC-99-0039 | TSA | $\geq 3.5 \times 10^4$ | $1.2 \times 10^4$ ($\geq 66\%$) | $3.0 \times 10^3$ ($\geq 91\%$) |
|  | SAB | $\geq 3.5 \times 10^4$ | $1.8 \times 10^4$ ($\geq 49\%$) | $4.1 \times 10^3$ $\geq 88\%$ |
| ROC-99-0040 | TSA | $1.0 \times 10^2$ | $\leq 12$ ($\geq 88\%$) | $\leq 12$ ($\geq 88\%$) |
|  | SAB | $\leq 9$ | $\leq 24$ | $\leq 12$ |
| ROC-99-0041 | TSA | $1.6 \times 10^3$ | $\leq 20$ ($\geq 98\%$) | $5.1 \times 10^2$ (68%) |
|  | SAB | $1.1 \times 10^3$ | $\leq 20$ ($\geq 98\%$) | $\leq 18$ ($\geq 98\%$) |

TABLE 3

Effect of Additional Incubation with Antibiotics After Enzymatic Dissociation

Bioburden (CFU/107 Cells) and Percent Reduction of Bioburden

| | | Dissociation with Gentamicin | | Dissociation with all Antibiotics | |
|---|---|---|---|---|---|
| Tumor ID | Medium | No Incubation | Additional Incubation | No Incubation | Additional Incubation |
| Roc-99-0035 | TSA | $\leq 9$ | 34 (>) | $\leq 9$ | $\leq 9$ |
|  | SAB | 90 | 17 (81) | 36 | 36 |
| Roc-99-0036 | TSA | $\leq 10$ | 139 (>>) | $\leq 10$ | $\leq 10$ |
|  | SAB | $2.4 \times 10^2$ | $1.8 \times 10^2$ (25) | $2.0 \times 10^2$ | 20 (90) |
| Roc-99-0037 | TSA | $\leq 6$ | $\leq 6$ | $\leq 6$ | $\leq 6$ |
|  | SAB | $\leq 6$ | $\leq 6$ | 12 | $\leq 6$ |

TABLE 3-continued

Effect of Additional Incubation with Antibiotics After Enzymatic Dissociation

Bioburden (CFU/10⁷ Cells) and Percent Reduction of Bioburden

| Tumor ID | Medium | Dissociation with Gentamicin | | Dissociation with all Antibiotics | |
| --- | --- | --- | --- | --- | --- |
| | | No Incubation | Additional Incubation | No Incubation | Additional Incubation |
| Roc-99-0038 | TSA | $1.4 \times 10^2$ | 82 (41) | 23 | 23 |
| | SAB | $1.1 \times 10^2$ | 82 (25) | 56 | 79 (>) |

Example 4

Irradiation of Dissociated Tumor Cells

To assess the feasibility of increasing the radiation dose, vials of cryopreserved dissociated tumor cells were irradiated while frozen (on dry ice) to a dose of 20,000 rads (approximately one hour) or 200,000 rads (approximately 10 hours). The cells were returned to liquid nitrogen storage until assaying. The vials were then quick thawed and the cells were assayed for viability; potency; and, depending upon the previously tested bioburden, sterility, bioburden or both. No differences in viability or potency were observed between the cells irradiated at different radiation doses (data not shown).

As may be seen from Table 4, with one exception, the bioburden was significantly reduced following irradiation at 200,000 rads. Of the five tumors that were tested, three were rendered sterile by the higher dose of irradiation. The other two tumors showed a marked reduction in bioburden. Inexplicably, one sample (patient ROC-00-0013) irradiated for 200,000 rads had a higher bioburden (40 CFU) than the sample that had received 20,000 rads (8 CFU); by contrast, the number of colonies of anaerobic bacteria was dramatically lower ($\leq 2$ CFU) at 200,000 rads than at 20,000 rads (168 CFU).

Although in vitro studies have demonstrated that no discernible differences in the essential biological characteristics exist between cells exposed to the two radiation doses and processed by the multistep process, to confirm this we assessed the effect upon the immunogenicity of the irradiated cells in the guinea pig hepatocarcinoma model that served as the foundation for clinical studies (Example 5). The interim results of a bioequivalence phase I-II study are provided in Example 6.

Example 5

Efficacy of Line 10 Vaccine Cells Prepared by the Sterile Oncovax® Process Invention to Protect Guinea Pigs from a Tumor Cell Challenge The purpose of this study was to determine whether the preferred process designed to render human colon tumor vaccines sterile results in an efficacious product. This experiment presents the methods and the results of a study designed to evaluate the effect of the sterilization process of the present invention upon the ability of the dissociated, irradiated cells to protect guinea pigs from a fatal dose of transplanted L-10 cells. In contrast to the historical method of tumor cell preparation, the improved process included washing tumors with 1% Triton X-100, disinfecting them with 0.4% Clorpactin®, performing the enzymatic dissociation in the presence of antibiotics/anti-mycotic drugs (gentamicin, Primaxin®, Levaquin®, and amphotericin B), and irradiation with 200,000 rads. The impact of these process changes upon vaccine efficacy was assessed in the same guinea pig active-specific immunotherapy model that was used for all of the pre-clinical studies that resulted in the development of the OncoVAX® product.

Two types of test materials were generated to perform this study: ascites cells and solid tumors. The ascites cells were used to generate solid tumors for the comparative immunization study. The ascites cells were also used to challenge the immunized animals. Solid tumors were produced by intramuscular injection of Line 10 (L-10) ascites cells. The resultant solid tumors were excised, processed and dissociated by either the original or improved sterile manufacturing process. The cells were then cryopreserved by controlled rate freezing. The cells were irradiated with either 20,000 or 200,000 rads.

TABLE 4

The Effect of Irradiation Upon Bioburden and Sterility

| Sample | Radiation Dose | Bioburden (CFU/mL) | | | Sterility | |
| --- | --- | --- | --- | --- | --- | --- |
| | | TSA (Aerobic) | TSA (Anaerobic) | SAB | Thioglycollate | Tryptic Soy Broth |
| Roc-00-0006 | 20,000 | 4 | 90 | $\leq 2$ | F | P |
| | 200,000 | $\leq 2$ | $\leq 2$ | $\leq 2$ | P | P |
| Roc-00-0007 | 20,000 | ND | ND | ND | F | P |
| | 200,000 | ND | ND | ND | P | P |
| Roc-00-0009 | 20,000 | ND | ND | ND | F | F |
| | 200,000 | ND | ND | ND | P | P |
| Roc-00-0010 | 20,000 | 13,600 | 14,000 | 644 | ND | ND |
| | 200,000 | 500 | 888 | 148 | ND | ND |
| Roc-00-0013 | 20,000 | 8 | 168 | ND | ND | ND |
| | 200,000 | 40 | $\leq 2$ | ND | P | F |

Ten strain 2 guinea pigs (five male and five female) were immunized twice (on a weekly basis) by the intradermal route with one of the following:
1. Cells produced by the original method, irradiated with 20,000 rads and admixed with BCG, or
2. Cells produced by the revised sterile method, irradiated with 200,000 rads and admixed with BCG, or
3. BCG alone.

Three weeks after completion of the immunization regimen, the animals were challenged intradermally with $10^7$ non-irradiated L-10 ascites cells. This highly tumorigenic dose was selected in order to more fully challenge the animals' anti-tumor responses and thereby demonstrate any differences between the two methods of vaccine preparation. The nodule diameter at each challenge injection site was measured and tumor progression was consequently determined. At 22 days after challenge, the animals treated with BCG had nodules that measured 20 mm in diameter. These animals were euthanized, together with all animals whose tumors had definitively progressed or regressed. There were four animals whose tumor progression/regression was equivocal. These animals were observed until day 28.

All of the animals that were immunized with BCG alone developed tumors that progressed unabated. Tumors progressed in one of ten animals previously immunized with cells produced and irradiated according to both the original and improved methods. Thus, the improved sterile production method did not affect the ability of the vaccine cells to confer protection from tumor challenge and hence did not adversely affect the immunogenicity of the L-10 guinea pig hepatocarcinoma cells. Based upon these results, it is our conclusion that the new sterile process designed to render human colon tumors sterile will produce vaccines that are as efficacious as the vaccines manufactured by the original OncoVAX® process.

Two L-10 tumor cell preparations were used for the conduct of this study: ascites cells and solid tumors. The ascites cells were used to generate solid tumors for vaccination and to challenge the immunized animals with a tumor burden. Solid tumors were produced by intramuscular injection of L-10 ascites cells. The solid tumors were processed and dissociated by either the original or revised manufacturing process. The cells were irradiated with either 20,000 or 200,000 rads.

L-10 ascites cells were thawed and washed. Three guinea pigs (4 weeks old) were inoculated by the intraperitoneal route with $5\times10^6$ cells. In addition, four guinea pigs (4-9 weeks old) were injected subcutaneously with L-10 cells ($5\times10^6$ cells/site, 4 sites/animal). Animals were injected by the subcutaneous route to generate solid tumors for processing as it was believed that the tumors would grow locally with less of the discomfort that potentially accompanies intramuscular tumors. Furthermore, it was conjectured that fewer animals would be required to produce the quantity of tumors required for these studies. Unexpectedly, the animals that were subcutaneously injected with tumor cells developed pleural effusions and/or peritoneal ascites rather than localized tumors. These animals were subsequently euthanized without any tumor material being obtained. Ten days later, the animals that had been inoculated by the intraperitoneal route were euthanized, the ascites fluid was harvested and the cells were cryopreserved by controlled rate freezing. These freshly cryopreserved ascites cells were stored for future use to generate solid tumors for vaccine processing as well as for the tumor challenge phase of the studies Since the injection by the subcutaneous route was not satisfactory for the production of solid tumors for vaccine processing, the intramuscular route was used. L-10 cells were thawed and washed. Thirteen guinea pigs were injected intramuscularly, with $5\times10^6$ L-10 cells, in each thigh. Seventeen days later, the animals were euthanized. Eighteen tumors from 9 animals were excised (total weight 109.2 grams) and dissociated by the original procedure and eight tumors from four animals were excised (63.5 grams) and dissociated by the new sterile method.

The original procedure was as follows:

Each tumor was washed in situ with four 10-mL changes of sterile normal saline. The saline was squirted forcefully with a 25-mL pipette. The tumors were then excised, weighed and transported to the tumor-processing laboratory in HBSS containing gentamicin (50 µg/mL) (HBSS/G). The tumors were then processed by the original process used to produce the vaccines used in the phase III study. The tumors were rinsed with three changes of HBSS/G and trimmed free of non-tumor and necrotic material. The tumor pieces were fragmented and rinsed again with three changes of HBSS/G. The tumor fragments were weighed and subjected to three cycles of enzymatic dissociation in the absence of all antibiotics. None of the process solutions used after the dissociation step contained any gentamicin. The resulting cell viability was 96% and 90 vials at $1.2\times10^7$ cells/vial were obtained. The dissociated tumor cells were then cryopreserved.

The preferred new procedure was as follows:

Each tumor was washed four times in situ each with 10 mL of fluid dispensed forcefully with a 25-mL pipette. The first, third and fourth washes consisted of sterile normal saline. The second wash consisted of sterile 1% Triton X-100 prepared in normal saline. The tumors were then excised, weighed and transported to the tumor-processing laboratory in HBSS/G. The tumors were then processed by the revised sterile method. The tumors were rinsed with three changes of HBSS/G and trimmed free of non-tumor and necrotic material. The trimmed tumor pieces were treated (on an orbital shaker at 200 RPM) with 0.4% Clorpactin® (prepared in normal saline) for two minutes at room temperature and then rinsed with three changes of HBSS/G. The tumor pieces were then fragmented, rinsed three times with HBSS/G, weighed, and subjected to three cycles of enzymatic dissociation. The enzyme dissociation solution contained gentamicin, Primaxin®, Levaquin® and amphotericin B. The resulting cell viability was 94% and 50 vials at $1.2\times10^7$ cells/vial were obtained. The cells were cryopreserved.

The frozen vials of cells were then irradiated. Cells obtained by the original dissociation process were irradiated with 20,000 rads. Cells obtained by the revised dissociation process were irradiated with 200,000 rads. After irradiation, red identification liners were inserted into the caps of vials that were irradiated with 200,000 rads. Vials irradiated with 20,000 rads were fitted with yellow identification cap liners.

As the Line 10 hepatocarcinoma cells are syngeneic with Sewall-Wright strain 2 guinea pigs, all of the test animals were of this strain. Each guinea pig received its first immunization (0.2 mL) administered intradermally above and behind the right axillary area. Each group was comprised of 10 animals (5 females and 5 males). Animals in group C were injected with cells produced by the original method, irradiated with 20,000 rads and admixed with BCG ($1\times10^7$ CFU). Group E animals were injected with cells produced by the new method, irradiated with 200,000 rads and admixed with BCG ($1\times10^7$ CFU). Finally, the guinea pigs in group F were injected with BCG ($1\times10^7$ CFU) alone. Six days later, the induration at each vaccination site was measured (in two diameters) with a calibrated caliper (Table 5).

The guinea pigs received the second immunization which was identical to the first immunization with the exception that it was administered above and behind the left axillary area. Six days later, the induration at each of the second vaccination sites was measured (in two diameters) with a calibrated caliper (Table 5).

All of the animals were challenged with viable, non-irradiated, L-10 cells obtained from ascites tumors. The challenge injection was given 21 days after the second immunization and was comprised of $1 \times 10^7$ non-irradiated cells (in 0.2 mL) administered intradermally. Forty hours later, the induration at the challenge injection site was measured (two diameters) with a calibrated caliper (Table 6).

The guinea pigs were observed daily for mortality and moribundity. Following the injection with non-irradiated tumor cells, the challenge injection sites were measured, twice weekly (two diameters), with a calibrated caliper. The Bonferroni Test (one-way Analysis of Variance [ANOVA]) was used to evaluate the statistical significance of any differences in the treatment groups.

As seen in Table 5, no significant differences were observed in the magnitude of induration measured six days after each immunization with the various preparations of cells admixed with BCG or with BCG alone. By contrast, the animals that had been vaccinated with tumor cells admixed with BCG had significantly greater responses to the challenge injection of non-irradiated tumor cells (induration measured 48 hours later) than did the animals vaccinated with BCG alone (Table 6). This indication of the development of cellular immunity to the tumor cells was borne out by the fate of the animals challenged with tumor cells (Table 6, FIG. 1). All of the ten animals that had been injected with BCG alone (group F) developed tumors that progressed unabated during the three week observation period; none were able to reject the challenge tumor cells. When measured 22 days after challenge injection, the average diameter of the tumors in animals in group F (18.8 mm [±1.05 mm]) was significantly larger than the nodules in the vaccine-treated groups. The average tumor size in animals in this group was also significantly larger than the other three groups when measured on days 11 and 18. One of ten guinea pigs vaccinated with BCG admixed with either L-10 cells dissociated by the original process and irradiated with (20,000 rads) (group C) or L-10 cells dissociated by the new method and irradiated with (200,000 rads) (group E) had a progressing tumor. The other nine animals in each of these two groups were able to reject the challenge of $10^7$ non-irradiated tumor cells. At day 22, the average diameters of nodules at the challenge site were 1.3 mm (±4.1 mm) and 3.6 mm (±6.1 mm) for groups C and E, respectively. This difference in tumor size was not significant; furthermore, no significant differences between groups C and E were observed at the other time points. On day 22, the study had met one of the protocol criteria for termination (when tumors reached 2 cm in diameter). At this point, the fate of the tumors in all of the animals, but two, could be unequivocally determined and the majority of the animals were euthanized. The two guinea pigs in question (group E #684, #689) had tumors that were either static or that were regressing very slowly. These animals were observed until day 28 (the second protocol criterion for study termination). On day 25, the tumor that had been regressing very slowly (animal #689) had disappeared entirely; the other animal's (#684) tumor continued to be arrested and non-progressing. When examined on day 28, the tumor (animal E#684) had also been rejected completely.

The animals in this study were challenged with a high dose of viable non-irradiated L-10 cells to detect potentially small differences in the immunogenicity of the vaccine cells. Although a dose response curve was not included in this study, historically, when $10^6$ L-10 cells were injected intradermally into naive strain 2 guinea pigs 100% of the animals died in 60-90 days because of metastases to vital organs. In this study, the challenge dose was 10-fold higher. Regardless of the process used, all of the L-10 vaccines conferred statistically significant protection, as compared to BCG alone, against a subsequent tumor cell challenge. No differences were observed in tumor progression in animals treated with vaccines produced by either the original (group C) or revised (group E) procedures.

In summary, the original manufacturing process was modified at several steps to reduce the concentration of enteric microorganisms endogenous to colon tumors and therefore render the autologous vaccines sterile. While in vitro studies (such as viability, identity and potency) have their value and have not demonstrated any differences between cells obtained by the two manufacturing processes, it is the immunogenicity of the vaccine cells that is the critical criterion for efficacy. As determined by the protection from a high dose of L-10 tumor cells, there were no differences in the immunogenicity of L-10 cells isolated and treated by either the original or improved sterilization processes. Inasmuch as the L-10 hepatocarcinoma-Strain 2 guinea pig model was the preclinical foundation for the clinical application of Onco-VAX®, it is our conclusion that human colon tumors processed by the new method will be equally efficacious.

TABLE 5

Induration (average [mm] of 2 diameters) of Vaccination Sites Measured 6 Days After Injection

| Group | Animal # | Vaccination Site #1 | Vaccination Site #2 | Group | Animal # | Vaccination Site #1 | Vaccination Site #2 |
|---|---|---|---|---|---|---|---|
| Group F | 657 | 12 | 11.5 | Group E | 682 | 13 | 15.5 |
| BCG Alone | 658 | 12 | 12.25 | Revised | 683 | 14.5 | 14.5 |
| | 659 | 12 | 13 | Process | 684 | 14.75 | 14 |
| | 660 | 13.5 | 14.25 | 200,000 rads | 685 | 13.75 | 14 |
| | 661 | 13.75 | 11.5 | | 686 | 15.25 | 15.5 |
| | 662 | 11.25 | 13.5 | | 687 | 12.75 | 15.5 |
| | 663 | 10.75 | 14 | | 688 | 13.5 | 16.25 |
| | 664 | 10.5 | 12.25 | | 689 | 14.5 | 15.75 |
| | 665 | 9.75 | 12.25 | | 690 | 15.25 | 14.25 |
| | 666 | 9.25 | 12.5 | | 691 | 11.5 | 13.15 |
| Group C | 626 | 12 | 13 | | | | |
| Original | 627 | 11 | 14 | | | | |
| Process | 628 | 8.75 | 11.25 | | | | |
| 200,000 rads | 629 | 10 | 14 | | | | |
| | 630 | 12 | 16.25 | | | | |

TABLE 5-continued

Induration (average [mm] of 2 diameters) of Vaccination Sites Measured 6 Days After Injection

| Group | Animal # | Vaccination Site #1 | Vaccination Site #2 | Group | Animal # | Vaccination Site #1 | Vaccination Site #2 |
|---|---|---|---|---|---|---|---|
| | 631 | 14.25 | 13.5 | | | | |
| | 632 | 13.5 | 14.5 | | | | |
| | 633 | 12.5 | 13.5 | | | | |
| | 634 | 12.5 | 14.25 | | | | |
| | 635 | 12 | 14.75 | | | | |

TABLE 6

Progression of L-10 Tumors Initiated by Challenge Injection of Non-Irradiated Cells

| Group | Animal # | Nodule Size (average [mm] of 2 diameters) Days After Challenge | | | | | | | Tumor Progression |
|---|---|---|---|---|---|---|---|---|---|
| | | 2 | 7 | 11 | 15 | 18 | 22 | 25 | 28 | |
| Group F BCG Alone | 657 | 12.5 | 12.75 | 14.75 | 14.25 | 16.75 | 17.5 (P) | | | 10/10 |
| | 658 | 10.75 | 16 | 14.75 | 15.5 | 18.5 | 19.75 (P) | | | |
| | 659 | 10 | 14.5 | 15.25 | 16.25 | 16.25 | 18 (P) | | | |
| | 660 | 12.5 | 13.25 | 15.25 | 16 | 18 | 18 (P) | | | |
| | 661 | 11.25 | 12 | 13.5 | 14.5 | 16.75 | 19.25 (P) | | | |
| | 662 | 12.25 | 13.25 | 14.5 | 16 | 17.5 | 18.25 (P) | | | |
| | 663 | 12 | 13.5 | 13.5 | 14 | 16.5 | 17.75 (P) | | | |
| | 664 | 13.25 | 14.25 | 15.75 | 16.75 | 19 | 20.5 (P) | | | |
| | 665 | 10.5 | 13.25 | 14.25 | 15 | 18 | 20 (P) | | | |
| | 666 | 13 | 12.5 | 14 | 14.5 | 17.5 | 18.5 (P) | | | |
| Group C Original Process 20,000 rads | 626 | 16.5 | 12.5 | 11.5 | 8.5 | 0 | 0 | | | 1/10 |
| | 627 | 15.25 | 12.5 | 9.75 | 7.5 | 0 | 0 | | | |
| | 628 | 14.5 | 13 | 13.75 | 10.5 | 11.5 | 13 (P) | | | |
| | 629 | 14.25 | 12.75 | 10.25 | 7 | 0 | 0 | | | |
| | 630 | 16.25 | 14.25 | 12.5 | 7.5 | 0 | 0 | | | |
| | 631 | 15.25 | 11.75 | 11.25 | 7.5 | 0 | 0 | | | |
| | 632 | 14.25 | 11.5 | 10 | 8.25 | 7.25 | 0 | | | |
| | 633 | 14.75 | 12.5 | 12 | 7.5 | 0 | 0 | | | |
| | 634 | 15 | 13 | 10.75 | 7 | 0 | 0 | | | |
| | 635 | 15.5 | 13.25 | 10 | 7.75 | 7.5 | 0 | | | |
| Group E Revised Process 200,000 rads | 682 | 18 | 12 | 11.75 | 8.75 | 9.75 | 0 | | | 1/10 |
| | 683 | 18 | 13.25 | 12.5 | 8.25 | 8 | 0 | | | |
| | 684 | 15.5 | 14.75 | 13.5 | 11.5 | 11.5 | 11.25 | 11.25 | 0 | |
| | 685 | 14.25 | 13.75 | 11 | 8.25 | 8.25 | 0 | | | |
| | 686 | 17.25 | 14 | 11 | 8.25 | 0 | 0 | | | |
| | 687 | 16.25 | 14.75 | 12 | 8.75 | 7.25 | 0 | | | |
| | 688 | 19 | 12.5 | 10.25 | 7.75 | 0 | 0 | | | |
| | 689 | 18.25 | 14.25 | 13 | 10.75 | 9.25 | 9 | 0 | | |
| | 690 | 13.25 | 13.75 | 13 | 13.25 | 14 | 16 (P) | | | |
| | 691 | 15 | 11.5 | 11 | 9 | 9.25 | 0 | | | |

(P) Progressing Tumor

Example 6

Impact of the Sterile Process Upon Vaccine Quality and Clinical Efficacy

Interim Results of a Phase I/II Bioequivalence Study

A bio-equivalence study was initiated. To date, twelve (12) patients have been treated with OncoVAX® that was manufactured by the improved sterile process.

The critical factors for vaccine efficacy are the absolute number of viable tumor cells and the condition of the cells. The cells must be able to persist at the vaccination site during a critical period for the development of the immune response. Consequently, the cells must be viable and metabolically active. These critical parameters serve the framework for the acceptance specifications (Table 7). Additionally, an identity assay to ensure that the cells are of adenocarcinoma origin is part of the panel of QC tests. Safety is assured by testing for endotoxin and sterility.

Several of these specifications were made more stringent after the introduction of the sterilization process. The specification for viability was increased from $\geq 70\%$ to $\geq 80\%$, the specification for potency was increased from $\geq 70\%$ to $\geq 90\%$ and the specification for sterility was changed from "for information" to no growth.

Thirty-two colon tumors were treated as described in the Examples above and, when tested for sterility by a duly validated sterility assay, twenty-six of the preparations were sterile (81%). Based upon previous data, it would be expected that had these tumors been processed by the original procedures of the '596 patent, none of the 26 tumors would have resulted in sterile OncoVAX® preparations.

The third and fourth vaccinations are comprised of irradiated, viable sterile, autologous tumor cells administered without the addition of the adjuvant BCG. As a consequence, any delayed cutaneous hypersensitivity (DCH) reactions (induration) are indicative of the patients' cellular immune responses to the vaccine cells. Data obtained from the phase III study indicated a correlation between size of the induration and clinical outcome. A positive clinical outcome was associated with induration measuring ≧5 mm in diameter observed at the site of the third (or fourth) injection 48 hours after injection. This criterion was accepted by the United States Food and Drug Administration for the performance of the bioequivalence study of sterile OncoVAX® vaccines.

Twelve of these sterile vaccine lots have been administered to patients, all of whom have received at least three treatments. None of the enrolled patients dropped out of the study once the first injection had been administered. The age of the patients ranged from 38-88, with a median age of 65.5. Five of the twelve patients were diagnosed with stage III colon cancer; the remaining seven patients were stage II. The specified range for the dosage is $0.7$-$1.3 \times 10^7$ viable tumor cells. The doses ranged from $0.76 \times 10^7$ to $1.3 \times 10^7$ viable tumor cells with an average dose of $0.99 \times 10^7$ (median=$0.98 \times 10^7$).

The sites of the third and fourth injections (dissociated tumor cells administered without BCG) were measured for induration (as well as for erythema) two days after inoculation. As is described in Table 8, all twelve patients that have received three vaccinations exhibited delayed cutaneous hypersensitivity (DCH) reactions to the third vaccination (tumor cells without BCG) that exceeded the criterion of ≧5 mm. Ninety-two percent (11 out of 12) had responses of at least one dimension of greater or equal to 10 mm. The average response was 14.6×13.4 mm. This is of note when it is compared to a previous phase III trial with 128 OncoVAX® treated patients where sterility of the product was rarely accomplished. In that trial, the majority of the vaccines had gastrointestinal microflora contamination. There was a DCH response ≧10 mm, measured 48 hours after the third vaccination, in 86.7% with an average induration of 17.3×18.0 mm. Thus, the present results indicate that sterile vaccines are immunogenic and that the immunogenicity is not primarily associated with microbial contaminants but rather is associated with tumor associated antigens.

Patients with stage II colon cancer receive the fourth treatment, on average, 20 weeks after the first inoculation. Stage III colon cancer patients were to receive the fourth vaccine approximately one month after completing chemotherapy. The two stage III patients treated thus far received the fourth immunization 32-36 weeks after the first treatment. Seven of the twelve patients described above have reached the time point for the fourth treatment. One of the seven patients did not receive a fourth treatment. Five of the six patients that have received four treatments exhibited significant DCH responses. Two of these highly responsive patients had stage III disease. Their responses were unaffected by the intervening course of chemotherapy and the 12-16 week delay in administration of the vaccine. The average response of these five to the fourth vaccination was 15.1×15.1 mm. The remaining patient, 568-003, had no demonstrable DCH reaction to the fourth vaccine. This stage II patient was younger (53) than average, received one of the highest vaccine doses ($1.24 \times 10^7$ viable tumor cells) and exhibited one of the strongest DCH reactions to the third vaccine (14.6 mm×16.1 mm). There is no plausible reason for the lack of responsiveness by this patient other than perhaps poor technique by the clinician administering the fourth vaccine.

The improved sterilization process, which includes treatment of the in situ colon tumor with detergent, disinfection of the dissected tumor with a disinfectant prior to digestion with a dissociation enzyme, exposure to antibiotics during dissociation, and irradiation with about 200,000 rads, had no negative impact on the essential biological characteristics previously shown to be critical for vaccine efficacy. Vaccine cells produced by the sterilization process were capable of eliciting an immune response exceeding the minimum specification that is correlated with a positive clinical outcome in every patient.

TABLE 7

Biological Product Release Tests

| Test Type | Test Method | Specification |
|---|---|---|
| Potency | Tumor cell Viability/Metabolic Activity | ≧80% |
|  | Viable Tumor Cell Number | ≧3.5 × 106 viable tumor cells/vial |
|  | Cellular esterase activity/potency assay | ≧90% of Trypan Blue excluding cells have intracellular esterase activity |
| Identity | Histopathology | Pathological confirmation of stage II or stage III adenocarcinoma of the colon |
|  | Immunofluorescence with 88BV59 tumor marker | Positive for tumor cells |
| Endotoxin | Kinetic Chromogenic Method | ≦150 EU/vial |
| Sterility | 21 CFR 610.12 | Negative for growth |

TABLE 8

Delayed Cutaneous Hypersensitivity Reactions Measured 48 Hours after the Third and Fourth Vaccinations.

| Patient ID | Age | Gender | Ethnic Origin | TNM Stage | Dose (× 107) | DCH 3rd Vaccine (mm × mm) | Interval Between 1st and 4th Treatments (weeks) | DCH 4th Vaccine (mm × mm) |
|---|---|---|---|---|---|---|---|---|
| 539-001 | 83 | F | 5 | III | 1.30 | 15.0 × 16.0 | 36.0 | 16.0 × 18.0 |
| 535-001 | 38 | M | 5 | II | 0.98 | 30.0 × 25.0 | 20.7 | 20.0 × 20.5 |
| 568-001 | 66 | F | 2 | III | 0.82 | 11.3 × 13.1 | 32.1 | 10.4 × 9.2 |
| 568-002 | 60 | F | 2 | III | 0.84 | 10.1 × 13.1 | — | ND |
| 539-002 | 65 | F | 5 | II | 0.85 | 9.0 × 10.0 | 19.7 | 11.0 × 15.0 |
| 568-003 | 53 | F | 5 | II | 1.24 | 14.6 × 16.1 | 20.0 | 0.4 × 0.4 |
| 539-003 | 63 | F | 5 | II | 1.10 | 12.0 × 10.0 | 22.1 | 18.0 × 13.0 |
| 539-004 | 69 | M | 5 | II | 0.98 | 11.0 × 11.0 | — | NA |
| 539-005 | 68 | M | 5 | II | 0.76 | 8.0 × 08.0 | — | NA |
| 539-006 | 81 | F | 5 | II | 1.24 | 20.0 × 13.0 | — | NA |

TABLE 8-continued

Delayed Cutaneous Hypersensitivity
Reactions Measured 48 Hours after the Third and Fourth Vaccinations.

| Patient ID | Age | Gender | Ethnic Origin | TNM Stage | Dose (× 107) | DCH 3rd Vaccine (mm × mm) | Interval Between 1st and 4th Treatments (weeks) | DCH 4th Vaccine (mm × mm) |
|---|---|---|---|---|---|---|---|---|
| 539-007 | 65 | F | 5 | III | 1.30 | 19.0 × 11.0 | — | NA |
| 539-008 | 88 | F | 5 | III | 0.80 | 15.0 × 14.0 | — | NA |

Ethnic Origin: 2 = Asian or Pacific Islander, 5 = White, not of Hispanic origin.
ND. Not done (this patient's fourth vaccine was accidentally destroyed at the hospital)
NA. Not Available (4th treatment not yet given)

All patents and publications cited herein are incorporated by reference. It should be readily understood that the invention is not limited to the specific embodiments described and illustrated above. Rather, the invention can be modified to incorporate any number of tumor cell types, cell dissociation techniques, disinfectants and washing procedures, antibiotics, and other variations, alterations, substitutions or equivalent arrangements not heretofore described, which are commensurate with the spirit and scope of the invention. For example, although the invention has been described with regard to certain preferred embodiments for carrying out the invention with regard to the sterile manufacture of colon tumor cell vaccines and the like, the invention may also be used to manufacture sterile renal carcinoma, lung carcinoma, and other solid tumor cell preparations that must be sterile, viable and non-tumorigenic. Accordingly, the invention is not limited by the foregoing description, but is only limited by the scope of the appended claims.

The invention claimed is:

1. A method for eliciting an immune response, comprising:
    excising solid tumor tissue from a cancer patient,
    processing the tumor tissue to reduce endogenous bioburden,
    digesting the tumor tissue with an enzyme to obtain viable dissociated tumor cells,
    irradiating said viable dissociated tumor cells at a dose of about 100,000 to 200,000 rads while frozen to render said viable tumor cells non-tumorigenic and sterile, and
    administering to said patient said viable sterile non-tumorigenic cells in a dose and a regimen sufficient to elicit an immune response.

2. The method of claim 1, wherein said irradiating is at a dose of at least 150,000 rads.

3. The method of claim 1, wherein said dose comprises about $10^7$ viable tumor cells and is comprised of a tumor cell population which is at least 80% viable.

4. The method of claim 3, wherein said treatment regimen begins 4-5 weeks after removal of the tumor and is comprised of at least three doses given at weekly intervals.

5. The meted of claim 4, wherein the first two of said three doses is combined with an adjuvant or immunostimulator.

6. The method of claim 4, wherein the patient is injected with a fourth dose five or more months after the first injection.

7. The method of claim 1, further comprising forceful washing of said tumor with a physiological solution prior to excision.

8. The meted of claim 7, further comprising washing said tumor with a detergent prior to excision.

9. The method of claim 8, wherein the detergent is selected from the group consisting of Triton X-100, NP40 and Tween 80.

10. The method of claim 1, further comprising the transport of said excised tumor in a physiological solution with antibiotics at a temperature of 0 to 6° C.

11. The method of claim 1, further comprising treatment of the tumor, after excision, with a disinfectant solution at a concentration and for a duration that provides anti-microbial activity while minimizing cytotoxicity.

12. The method of claim 11, wherein the disinfectant is selected from the group consisting of sodium oxychlorosene, sodium hypochlorite and stabilized chlorine dioxide.

13. The method of claim 1, wherein the enzyme is collagenase.

14. The method of claim 1, wherein the digesting is performed in the presence of at least one of an antibiotic and anti-mycotic agent to reduce bioburden.

15. The method of claim 14, wherein the antibiotic is selected from the group consisting of imipenem and levofloxacin.

16. The method of claim 1, wherein the tumor cells are cryopreserved after digestion by controlled rate freezing at about −1° C./minute to a temperature of about −80° C. and maintained in a cryogenic state until thawed prior to administering to the patient.

17. The method of claim 1, wherein the irradiating is in an amount of 190,000 or more rads.

* * * * *

UNITED STATES PATENT AND TRADEMARK OFFICE
CERTIFICATE OF CORRECTION

| | | |
|---|---|---|
| PATENT NO. | : 7,628,996 B2 | Page 1 of 1 |
| APPLICATION NO. | : 10/370081 | |
| DATED | : December 8, 2009 | |
| INVENTOR(S) | : Haspel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 939 days.

Signed and Sealed this

Second Day of November, 2010

David J. Kappos
*Director of the United States Patent and Trademark Office*